United States Patent
Haruta et al.

(10) Patent No.: US 9,533,285 B2
(45) Date of Patent: Jan. 3, 2017

(54) GOLD CLUSTER CATALYST AND METHOD FOR PRODUCING SAME

(71) Applicant: TOKYO METROPOLITAN UNIVERSITY, Tokyo (JP)

(72) Inventors: Masatake Haruta, Hachioji (JP); Yue Yu, Hachioji (JP); Jiahui Huang, Hachioji (JP); Ayako Taketoshi, Hachioji (JP); Tamao Ishida, Fukuoka (JP); Tomoki Akita, Tsukuba (JP); Atsushi Ogata, Tsukuba (JP); Hyun-Ha Kim, Tsukuba (JP)

(73) Assignee: TOKYO METROPOLITAN UNIVERSITY, Tokyo (JP)

( * ) Notice: Subject to any disclaimer, the term of this patent is extended or adjusted under 35 U.S.C. 154(b) by 0 days.

(21) Appl. No.: 14/407,279

(22) PCT Filed: Jun. 7, 2013

(86) PCT No.: PCT/JP2013/065816
§ 371 (c)(1),
(2) Date: Dec. 11, 2014

(87) PCT Pub. No.: WO2013/187323
PCT Pub. Date: Dec. 19, 2013

(65) Prior Publication Data
US 2015/0151279 A1    Jun. 4, 2015

(30) Foreign Application Priority Data

Jun. 12, 2012   (JP) ................................. 2012-133329

(51) Int. Cl.
*B01J 37/04*      (2006.01)
*B01J 23/02*      (2006.01)
(Continued)

(52) U.S. Cl.
CPC ............... *B01J 23/52* (2013.01); *B01J 21/066* (2013.01); *B01J 23/10* (2013.01); *B01J 23/66* (2013.01);
(Continued)

(58) Field of Classification Search
CPC ............. B01J 23/52; B01J 21/00; B01J 37/08; B01J 37/12; B01J 37/14; B01J 37/349
(Continued)

(56) References Cited

U.S. PATENT DOCUMENTS 7,727,931 B2 * 6/2010 Brey ........................ A62D 9/00
423/23
7,955,570 B2 * 6/2011 Insley .................. B01D 53/864
422/177

(Continued)

FOREIGN PATENT DOCUMENTS

JP    2004-500226 A    1/2004
JP    2007-090164 A    4/2007
(Continued)

OTHER PUBLICATIONS

Tatsuya Tsukuda et al., "Tanjikin Cluster Shokubai no Seimitsu Gosei to Size Tokuiteki Sanka Shokubai Kassei", Dai 105 Kai Shokubai Toronkai Toronkai A Yokoshu, Mar. 24, 2010, p. 124 with English translation, International Search Report of International Application No. PCT/JP2013/065816 mailed Sep. 10, 2013 (5 pages).

(Continued)

*Primary Examiner* — Cam N. Nguyen
(74) *Attorney, Agent, or Firm* — Westerman, Hattori, Daniels & Adrian, LLP

(57) ABSTRACT

A gold cluster catalyst is capable of promoting/controlling a chemical reaction with high catalytic activity and selectivity. The gold cluster catalyst has a carrier supporting clusters, (Continued)

each of which is an aggregate of a plurality of gold atoms, which can be obtained by providing the carrier supporting a plurality of gold cluster compounds and then processing the gold cluster compounds on the carrier, in which each of the gold cluster compounds is stabilized by an organic ligand and including a predetermined number of gold atoms. In the gold cluster catalyst, each of the clusters may have a particle diameter of 10 nm or less and be formed substantially only of gold atoms.

1 Claim, 7 Drawing Sheets

(51) Int. Cl.
| | |
|---|---|
| B01J 23/04 | (2006.01) |
| B01J 21/04 | (2006.01) |
| B01J 23/52 | (2006.01) |
| B01J 37/08 | (2006.01) |
| B01J 37/34 | (2006.01) |
| B01J 23/66 | (2006.01) |
| B01J 35/02 | (2006.01) |
| C07C 29/141 | (2006.01) |
| C07C 33/32 | (2006.01) |
| C07C 209/36 | (2006.01) |
| C07C 245/08 | (2006.01) |
| B01J 37/02 | (2006.01) |
| B01J 37/03 | (2006.01) |
| B01J 21/06 | (2006.01) |
| B01J 35/00 | (2006.01) |
| B01J 23/10 | (2006.01) |

(52) U.S. Cl.
CPC .......... *B01J 35/006* (2013.01); *B01J 35/0013* (2013.01); *B01J 35/02* (2013.01); *B01J 37/0211* (2013.01); *B01J 37/0234* (2013.01); *B01J 37/031* (2013.01); *B01J 37/08* (2013.01); *B01J 37/34* (2013.01); *B01J 37/349* (2013.01); *C07C 29/141* (2013.01); *C07C 33/32* (2013.01); *C07C 209/36* (2013.01); *C07C 245/08* (2013.01); *Y02P 20/52* (2015.11)

(58) Field of Classification Search
USPC ............................................ 502/5, 344, 439
See application file for complete search history.

(56) References Cited

U.S. PATENT DOCUMENTS

| | | | | |
|---|---|---|---|---|
| 7,989,384 | B2* | 8/2011 | Brey | A62D 9/00 423/427 |
| 8,053,387 | B2* | 11/2011 | Flytzani-Stephanopoulus | B01J 23/42 502/302 |
| 8,058,202 | B2* | 11/2011 | Brady | B01D 53/864 423/427 |
| 8,137,750 | B2* | 3/2012 | Brey | B01J 21/063 427/217 |
| 8,314,046 | B2* | 11/2012 | Brady | B01D 53/864 423/427 |
| 8,314,048 | B2* | 11/2012 | Brey | A62D 9/00 423/23 |
| 8,435,921 | B2* | 5/2013 | Matolin | B01J 23/63 502/304 |
| 8,518,854 | B2* | 8/2013 | Brady | B01D 53/864 423/23 |
| 8,618,020 | B2* | 12/2013 | Brey | A62D 9/00 423/23 |
| 8,664,148 | B2* | 3/2014 | Brey | A62D 9/00 502/184 |
| 8,664,149 | B2* | 3/2014 | Brady | B01D 53/864 502/184 |
| 2008/0260607 | A1* | 10/2008 | Flytzani-Stephanopoulos | B01J 23/63 422/222 |
| 2009/0054230 | A1* | 2/2009 | Veeraraghavan | A62D 9/00 502/344 |
| 2010/0273091 | A1* | 10/2010 | Brey | B01J 21/063 429/513 |
| 2012/0178616 | A1* | 7/2012 | Flytzani-Stephanopoulos | B01J 23/52 502/87 |
| 2013/0309158 | A1* | 11/2013 | Brey | A62D 9/00 423/245.1 |

FOREIGN PATENT DOCUMENTS

| | | |
|---|---|---|
| JP | 2007-301470 A | 11/2007 |
| JP | 2008-259993 A | 10/2008 |
| JP | 2010-510048 A | 4/2010 |
| JP | 2010-247108 A | 11/2010 |
| WO | 99/21652 A2 | 5/1999 |
| WO | 2008/063880 A1 | 5/2008 |

OTHER PUBLICATIONS

Taketoshi Matsumoto et al., "TiO2 (110) Joni Tanji shita Alkanethiolate Hogo Kin Cluster no Hairetsu no STM Kansatsu", the 86th Annual Meeting of the Chemical Society of Japan in Spring Koen Yokoshu I, Mar. 13, 2006, p. 311 with English translation, International Search Report of International Application No. PCT/JP2013/065816 mailed Sep. 10, 2013 (5 pages).
Masatake Haruta et al., "Novel Gold Catalysts for the Oxidation of Carbon Monoxide at a Temperature far Below 0 ° C.", The Chemical Society of Japan, 1987, pp. 405-408, (4 pages).
International Search Report of International Application No. PCT/JP2013/065816 mailed Sep. 10, 2013 (5 pages).

* cited by examiner

PPh₃
(Gold complex compound carrier)

Au₁₁/ZrO₂ (PL)
(Example 1)

Au₁₁/ZrO₂ (PL, 150)
(Example 7)

GOLD CLUSTER CATALYST AND METHOD FOR PRODUCING SAME

TECHNICAL FIELD

The present invention relates to a gold cluster catalyst and, more specifically, relates to a gold cluster catalyst comprising clusters of gold atoms that allows reactions to proceed with high selectivity.

BACKGROUND ART

Solid catalysts (Heterogeneous catalysts) have been industrialized in the early 20th century and since then have contributed to the development in the inorganic chemical industry, the coal chemical industry and the petrochemical industry. Solid catalysts can be generally classified into three categories according to the material system: metal sulphides used for hydrodesulphurization of petroleum, metal oxides used for selective oxidation of unsaturated hydrocarbons and metals used for purification of automobile emissions. Among others, noble metals have broad utility because they can be used for both oxidation and reduction reactions. Typical noble metals particularly include palladium and platinum.

Gold has been recognized as a metal that is particularly stable and thus has poor catalytic activity among noble metals. However, the present inventor found for the first time in the world that gold nanoparticles having a diameter of 5 nm or less exhibit superior catalytic activity when they are supported on oxides of base metals (Non Patent Literature 1). Gold nanoparticles exhibit high performance, which could not be attained by palladium or platinum catalysts, in CO oxidation at room temperature, gluconic acid synthesis by oxygen oxidation of glucose aqueous solution, hydrogen peroxide synthesis from hydrogen and oxygen, one-pot synthesis of azobenzene from nitrobenzene and the like.

Various catalysts containing noble metals have been proposed. For example, Patent Literatures 1 and 2 propose noble metal-containing catalysts having selectivity in specific types of reactions.

Patent Literature 1: Japanese Patent Application Laid-open No. 2007-301470
Patent Literature 2: Japanese Patent Application Laid-open No. 2007-90164
Non Patent Literature 1: M. Haruta, Chem. Lett. 1987

DISCLOSURE OF THE INVENTION

However, the above proposed catalysts still cannot control reactions with sufficient selectivity and cannot provide desired substances with high reactivity and with a reduced amount of byproducts. Therefore there is still a need for the development of catalysts that can control reactions with high selectivity.

Thus an object of the present invention is to provide a gold cluster catalyst and a method of producing same that allows promotion and control of chemical reactions with high catalytic activity and selectivity.

The present inventors have made intensive studies to achieve the above-described object. First, the present inventors presumed that a specific diameter or number of atoms may contribute to the exhibition of particularly superior performance with regard to the catalytic activity and selectivity of gold nanoparticles and clusters thereof. The present inventors have made intensive studies on that presumption and, as a result, found that by selecting an optimal diameter or a specific number of atoms in a catalyst containing naked gold nanoparticles and clusters which are not protected or stabilized by organic ligands and the like, the nanoparticles and clusters being dispersed and immobilized on a metal oxide, a carbon material or a polymer material, an excellent catalytic activity and/or selectivity can be obtained for various chemical reactions. According to the further intensive studies carried out by the inventors, they have successfully produced a gold cluster catalyst carrying a gold cluster which is formed only of gold atoms and from which particularly an organic ligand has been removed, and found that the gold cluster catalyst can achieve the above object. Thus, the inventors have completed the present invention.

Namely the present invention provides the following aspects.

1. A gold cluster catalyst comprising a plurality of clusters of gold atoms supported on a carrier, wherein the clusters are formed by allowing a plurality of gold cluster compounds having a predetermined number of gold atoms that are stabilized by an organic ligand to be supported on the carrier and then treating it to treatment,
wherein the cluster has a particle diameter of 10 nm or less and substantially consists of gold atoms.

2. The gold cluster catalyst according to claim 1, wherein the clusters substantially consisting of the gold atoms have a removal rate of the organic ligand of 90% or more.

3. The gold cluster catalyst according to claim 1 or 2, wherein the number of the gold atoms in each of the clusters is selected from the group consisting of 11, 13, 55, 101 and 147.

4. The gold cluster catalyst according to any of claims 1 to 3, wherein the carrier is ceria or zirconia.

5. The gold cluster catalyst according to any of claims 1 to 4, which is used as a hydrogenation catalyst of an oxygen atom-containing organic compound.

6. A method of producing the gold cluster catalyst according to claim 1, the method comprising:
allowing a carrier to carry a plurality of gold cluster compounds respectively having a predetermined number of gold atoms that are stabilized by an organic ligand, and subjecting the gold cluster compounds on the carrier to an oxygen plasma treatment.

7. The method of producing the gold cluster catalyst according to claim 6, further comprising, after the plasma treatment, firing the gold cluster compounds on the carrier in air at a temperature ranging of 100° C. to 800° C.

A gold cluster catalyst comprising clusters of gold atoms (referred as "gold cluster catalyst" hereinbelow) of the present invention allows synthesis of various compounds with high selectivity.

A method of producing the gold cluster catalyst of the present invention can produce the gold cluster catalyst which has the controlled number of gold atoms and from which an organic ligand has been removed, thereby being formed substantially only of gold atoms.

EMBODIMENTS OF THE INVENTION

Figure 1:
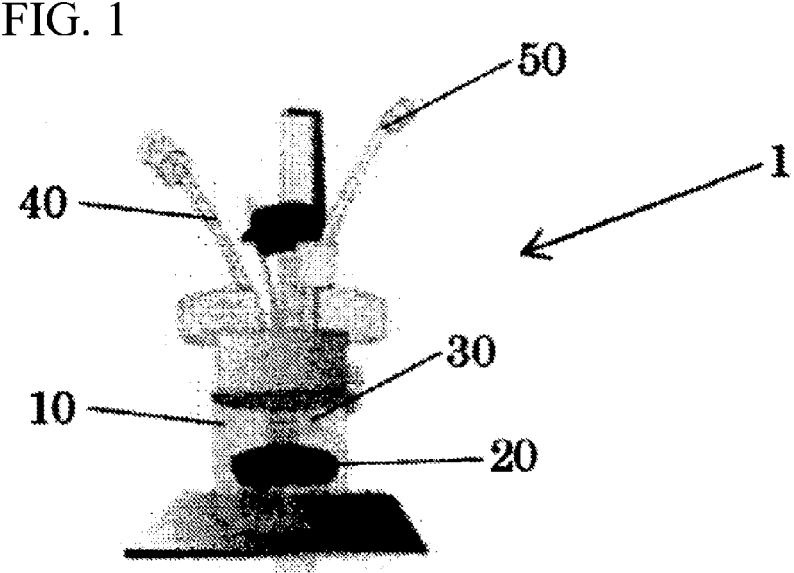
FIG. 1 is a perspective view schematically showing an oxygen plasma processing device used for production of a gold cluster catalyst of the present invention.

The present invention is further specifically described hereinbelow.

A gold cluster catalyst (first aspect) of the present invention comprises clusters of gold atoms supported on a carrier, wherein the clusters are formed by allowing a plurality of gold cluster compounds having a predetermined number of gold atoms that are stabilized by an organic ligand to be supported on the carrier and then treating it to treatment, the cluster has a particle diameter within a specific range and substantially consists of the gold atoms.

The gold cluster catalyst of the present invention is further specifically described hereinbelow.

<Carrier>

The carrier is not particularly limited as far as it can carry a gold nanoparticle formed of from 200 to a few tens of thousands of gold atoms assembled or a gold cluster formed of 200 or less atoms assembled. Specific examples of the component thereof include oxides and complex oxides of base metals such as $MgO$, $Al_2O_3$, $SiO_2$, $CaO$, $TiO_2$, $V_2O_5$, $Cr_2O_3$, $MnO_x$, $Fe_2O_3$, $CO_3O_4$, $NiO$, $CuO$, $ZnO$, $SrO$, $ZrO_2$, $Nb_2O_5$, $MoO_3$, $SnO_2$, $BaO$, $La_2O_3$, $CeO_2$, $Bi_2O_5$ and $CeO_2$—$ZrO_2$ (weight ratio 1:1, 1:3).

Among these, $ZrO_2$ (zirconia) and $CeO_2$ (ceria) are particularly preferable. Particularly ceria is preferable because it is known that it has strong interaction with gold clusters, can carry gold clusters as they are (in the state such that the clusters should be) without aggregation thereof and thus allows unique catalytic activity. Ceria may be a commercially available product including, for example, $CeO_2$-1 available from Shin-Etsu Chemical Co., Ltd. of BET (specific surface area, $m^2/g$) 161, $CeO_2$-2 available from Daiichi Kigenso Kagaku Kogyo Co., Ltd. of BET 166 and $CeO_2$-3 available from Sakura Co., Ltd. of BET 25.4. The carrier used may be a metal oxide having regular porous structures including, for example, titanosilicalite-1 (TS-1) having micropores of 2 nm or less and MCM-41 and SBA-15 which are silica having mesopores of 2 nm or larger.

The carrier may have any shape including a sphere, a plate, a flower and a rod.

In terms of the size, the carrier preferably has an average particle diameter of 1 nm to 1 µm and more preferably 10 nm to 100 nm. Alternatively the size of the carrier is preferably 4 to 20 times of the particle diameter of the gold clusters to be supported on the carrier. The carrier of plate-shaped, flower-shaped, or rod-shaped preferably has a thickness of 5 nm to 100 nm.

<Gold Clusters>

The gold cluster catalyst of the present invention is characterized in that it includes the gold clusters having a particle diameter of 10 nm or less, preferably 0.8 to 5.0 nm and particularly preferably 0.8 to 2.0 nm. The particle diameter in this context means the longest particle diameter of a gold cluster particle.

When the particle diameter is higher than 10 nm, the catalytic activity is decreased, and thus the particle diameter is required to be within the above range. As used herein, the phrase in the context that the gold cluster supported on the carrier "substantially consists of gold atoms" means a gold cluster from which at least 90%, preferably 95% of organic ligand has been removed (based on the number of the organic ligand molecules originally introduced).

The gold clusters are an assembly of gold atoms formed by processing a plurality of gold cluster compounds supported on the carrier, each of the gold cluster compounds having a predetermined number of gold atoms that are stabilized by an organic ligand. By the processing, the organic ligand is removed and the gold clusters formed only of gold atoms are supported on the carrier. By removing the organic ligand as described above, inhibition on the catalytic activity by the organic ligand is eliminated, resulting in a further increased catalytic activity.

The predetermined number of atoms is preferably selected from the group consisting of 11, 13, 55, 101 and 147, and particularly preferably selected from the group consisting of 11, 55 and 101.

The gold cluster formed only of gold atoms is not particularly limited in terms of the shape thereof and the like as far as the cluster is formed only of the predetermined number of gold atoms. However the gold cluster preferably has the shape of a hemisphere such that the gold cluster can closely attach to the carrier in order to have thermally stable properties.

(Overall Configuration of Gold Cluster Catalyst)

In the gold cluster catalyst of the present invention including the gold clusters supported on the carrier, the gold clusters are fixed on the carrier by means of interaction between the gold clusters and the carrier.

The gold cluster catalyst is not particularly limited in terms of the size or shape of the whole catalyst as far as the catalyst is formed of the carrier and the gold cluster. However the catalyst preferably has an average particle diameter of 1 nm to 10 nm.

The gold cluster catalyst preferably has a weight ratio between the gold atoms and the carrier such that the gold atoms account for 0.1 to 5.0 parts by weight relative to 100 parts by weight of the carrier.

<Method for Producing>

A method for producing the gold cluster catalyst of the present invention can be carried out by allowing a carrier to carry a plurality of gold cluster compounds respectively having a predetermined number of gold atoms that are stabilized by an organic ligand, and subjecting the carrier carrying the gold cluster compounds to a plasma processing step including oxygen plasma processing.

The method is further described hereinbelow.

(Preliminary Step)

In the present invention, a gold cluster compound production step can be carried out prior to the plasma processing step, in which a gold cluster compound having a predetermined number of gold atoms that are stabilized by an organic ligand is produced.

The gold cluster compound production step can be carried out by, for example, reaction of a halogenated gold compound such as chloroauric acid tetrahydrate with a series of phosphine compounds such as triphenylphosphine at 0 to 50° C.

In order to obtain a desired number of gold atoms in the gold cluster compound production step, well known synthetic methods can be used depending on the number of atoms desired. For example, in order to obtain a chloro(triphenylphosphine) $Au_{11}$ cluster (a cluster of $Au_{11}$ protected with phosphine; the number written as a subscript to the right of Au as in $Au_{11}$ indicates hereinbelow the number of gold atoms in a cluster) having the number of gold atoms of 11, chloro(triphenylphosphine)Au is allowed to react with sodium borohydride, and in order to obtain an $Au_{55}$ cluster, chloro(triphenylphosphine)Au is allowed to react with borane-tetrahydrofuran (THF) complex ($BH_3$-THF complex), and in order to obtain an $Au_{101}$ cluster, triphenylphosphine is added to a reaction solution of chloroauric acid and tetraoctylammonium bromide (TOAB).

(Plasma Processing Step)

Examples of the gold cluster compound obtained from the preliminary step and having a predetermined number of gold atoms include a phosphine-protected $Au_{11}$ cluster, a phosphine-protected $Au_{101}$ cluster and the like.

Examples of a method for allowing the carrier to carry the gold cluster compounds include a dry mixing method and a wet mixing method.

The solid phase mixing method can be carried out by mixing the gold cluster compound and the carrier in a mortar and the like and subjecting the mixture to firing in air at 100 to 400° C. for 1 to 10 hours in an electric furnace.

The wet mixing method can be carried out by mixing the carrier and the gold cluster compound in a system to which a solvent is added on a mixing device such as a ball mill and subjecting the mixture to firing in air at 100 to 400° C. for 1 to 10 hours in an electric furnace.

The production method of the present invention is characterized in that a plasma processing step is carried out in which a gold cluster compound-carrying substance obtained by allowing the carrier to carry the gold cluster compounds is subjected to oxygen plasma processing.

Namely it is preferable that the gold cluster catalyst of the present invention is obtained by allowing a carrier to carry a gold complex compound having a predetermined number of gold atoms and subjecting the carrier carrying the gold complex compound to the plasma processing as described above.

The plasma processing may be carried out on a device shown in FIG. 1, for example.

A device 1 shown in FIG. 1 includes a reaction vessel 10, a sample stage 20, a plasma spray 30, an oxygen inlet tube 40 and an aspiration tube 50 for aspirating air in the vessel. Such a device is based on the principle of plasma processing disclosed in Japanese Patent Application Laid-open Nos. 2008-49282, 2008-49280 and the like.

A sample mounted on the sample stage 20 is irradiated with plasma under the conditions of a frequency of 1 to 100 kHz, a voltage (input voltage) of 10 to 100 V (actual applied voltage is 10 kV to 20 kV) and power of 1 to 10 W while supplying oxygen through the oxygen inlet tube 40 and aspirating internal gas through the aspiration tube 50. The period for irradiation is arbitrary depending on the weight of the sample and is preferably 1 to 10 minutes per 1 g of the sample.

In the present invention, a firing step may be further carried out after the plasma processing step, in which firing in air is carried out at 100 to 800° C.

The firing in air is preferably carried out under the temperature condition of 100 to 800° C. and more preferably 200 to 400° C. When the temperature is lower than 100° C., the organic ligand may not be burnt out or removed which may result in the suppression of catalytic activities, while when the temperature is higher than 800° C., gold clusters or gold nanoparticles may be melted which may unfavourably result in the production of larger particles. The period for firing is preferably 1 to 10 hours and more preferably 2 to 4 hours.

The firing can be carried out in air using an electric furnace.

Hydrogen reduction may also be carried out. Particularly when the carrier is formed of a polymer material, hydrogen reduction is useful because the firing temperature may not be increased at or above 200° C. Hydrogen reduction may be carried out using a well known device under the following conditions:

Conditions:
Gas flow rate: 10 to 30 ml/min
$Ar:H_2$=30:1 to 0:1
Firing temperature: 100 to 400° C.
Period of temperature increase: 0.5 to 3 hours
Firing period: 1 to 3 hours (Post-Treatment Step)

The thus obtained gold cluster catalyst may be subjected to a post-treatment step by, for example, a purification treatment according to the methods generally used after obtainment of gold compounds.

<Method of Use>

As described above, the gold cluster catalyst of the present invention is a gold catalyst that includes clusters, which respectively are an assembly of a plurality of gold atoms, supported on a carrier, is obtained by allowing the carrier to carry clusters of gold complex compounds respectively including a predetermined number of gold atoms and subjecting the carrier with the clusters to plasma processing, and is preferably used as a hydrogenation catalyst of an oxygen atom-containing organic compound.

The method of use of the gold cluster catalyst of the present invention is described hereinbelow.

The gold cluster catalyst of the present invention can be used upon production of various compounds and allows production of desired compounds with high selectivity. Among others, the gold cluster catalyst of the present invention can be used as a hydrogenation catalyst of oxygen atom-containing organic compounds described hereinbelow.

(Hydrogenation of Cinnamaldehyde)

The gold cluster catalyst of the present invention is useful as a hydrogenation catalyst during production of cinnamyl alcohol (shown as 2 in the following chemical formula) by hydrogenation of cinnamaldehyde (1) according to the reaction shown in the following formula:

[Chemical Formula 1]

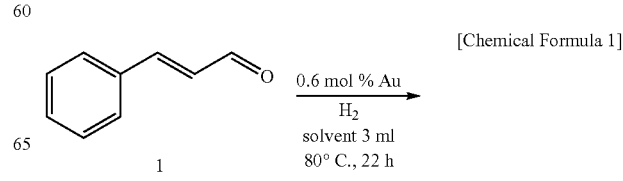

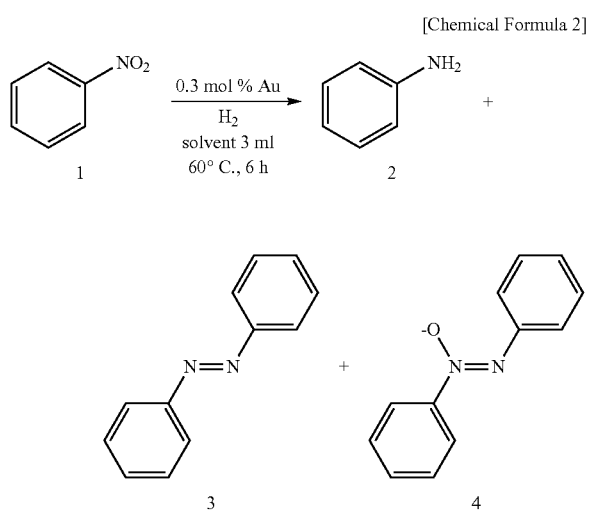

Particularly, a gold cluster catalyst including gold clusters respectively having the number of gold atoms of 101 is useful.

(One-Pot Synthesis of Azobenzene from Nitrobenzene)

The gold cluster catalyst of the present invention is useful as a catalyst for one-pot synthesis (a synthesis procedure for carrying out a multi-stage reaction by charging reactants at once or sequentially in one reaction vessel (generally a flask)) of azobenzene (3) from nitrobenzene (1) according to the reaction shown in the following formula:

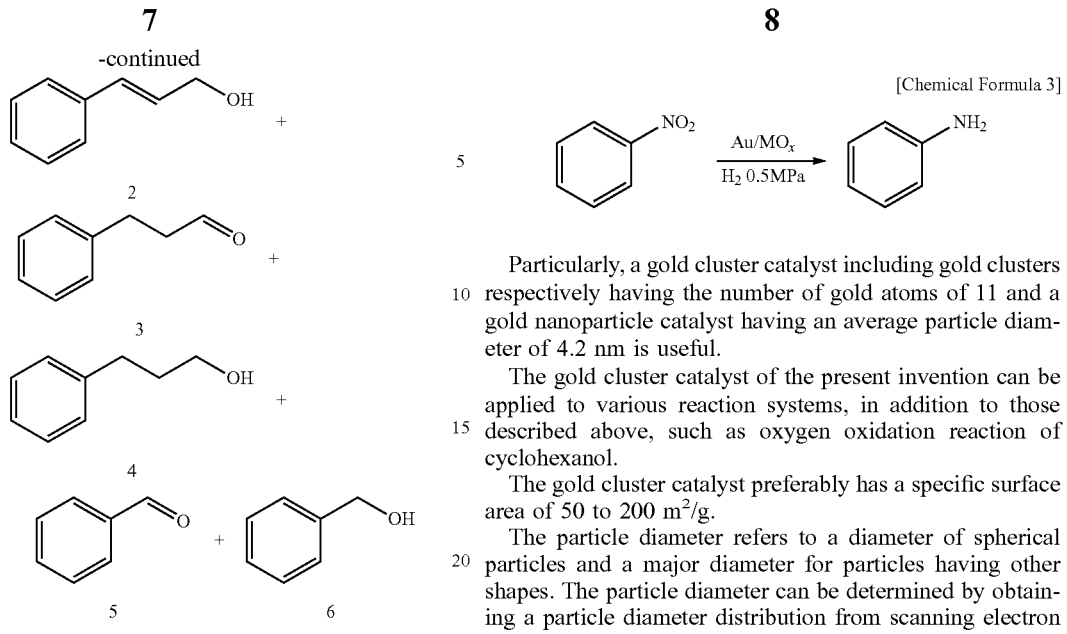

Particularly, a gold cluster catalyst including gold clusters respectively having the number of gold atoms of 11 is useful.

(Synthesis of Aniline by Hydrogenation of Nitrobenzene)

The gold cluster catalyst of the present invention is useful as a catalyst for synthesis of aniline from nitrobenzene according to the reaction shown in the following formula:

Particularly, a gold cluster catalyst including gold clusters respectively having the number of gold atoms of 11 and a gold nanoparticle catalyst having an average particle diameter of 4.2 nm is useful.

The gold cluster catalyst of the present invention can be applied to various reaction systems, in addition to those described above, such as oxygen oxidation reaction of cyclohexanol.

The gold cluster catalyst preferably has a specific surface area of 50 to 200 $m^2/g$.

The particle diameter refers to a diameter of spherical particles and a major diameter for particles having other shapes. The particle diameter can be determined by obtaining a particle diameter distribution from scanning electron microscopy (SEM) or transmission electron microscopy (TEM) and calculating an average therefrom.

<Third Component>

The gold cluster catalyst of the present invention may include a component other than the carrier and the gold clusters within the range that does not impair the desired effect of the present invention.

Conventional gold catalysts have been prepared by directly dispersing or immobilizing gold precursors on carriers, and thus a distribution in the diameter or thickness of gold nanoparticles has been unavoidable. Therefore, with regard to the effect of the dimension on catalytic characteristics (activity per molecule exposed on the surface and selectivity), it has been considered that smaller is generally better. However, when monodisperse (defined as standard deviation of within 10% for nanoparticles and defined at a level of one atom for clusters) gold nanoparticles or gold clusters are used, gold nanoparticles and gold clusters having dimensions (thickness and diameter) and the number of atoms (magic number) have been reported that exhibit particularly excellent catalytic characteristics. Under the current situation, no clear concept, methodology or method for production of catalyst samples has been proposed for the dimensional specificity.

Therefore under the current situation, there is a need for development of a gold nanoparticle catalyst and a method for producing the gold cluster catalyst in which the dimensions of gold can be defined as freely as possible and for identification of specific examples of reactions and systematization of the dimensional specificity.

EXAMPLES

The present invention is specifically described hereinbelow by way of Examples and Comparative Examples which do not limit the present invention.

Example 1

Preparation of Gold Cluster Catalyst Having the Number of Gold Atoms of 11

(Synthesis of chloro(triphenylphosphine)Au (I))

Chloroauric acid tetrahydrate (1 g) was dissolved in 35 mL of ethanol in a nitrogen atmosphere while stirring to give a chloroauric acid solution. To the chloroauric acid solution, 50 ml of an ethanol solution of 1.364 g triphenylphosphine was added in a nitrogen atmosphere and reaction was carried out. The color of the reaction solution was changed from yellow to white and a white precipitate was produced. The precipitate was dissolved in 5 ml of dichloromethane, 120 ml of pentane was gradually added to the dichloromethane solution. A mixture of pentane and the dichloromethane solution was stored in a freezer overnight to allow precipitation of a white substance which was then applied to suction filtration and drying in vacuo to give the product (chloro (triphenylphosphine)Au (I)).

(Synthesis of $Au_{11}$ Gold Cluster Compound)

The obtained chloro(triphenylphosphine)Au (I) (0.25 g) was dispersed in 20 g of dehydrated ethanol and the dispersion was stirred for 5 minutes. To the dispersion, 27 mg of sodium boronhydride was then added over 20 minutes and a mixture of the dispersion and sodium boronhydride was stirred for 2 hours. The product was added to hexane (125 ml) and a precipitate was formed over 20 hours. Then the mixture was added to a dichloromethane solution, filtered and dried to give phosphine-protected $Au_{11}$ clusters having the number of gold atoms of 11.

(Supporting onto Carrier)

Then the prepared $Au_{11}$ gold cluster compound (16 mg) was dispersed in 20 ml of $CH_2Cl_2$, 1.0 g of a $ZrO_2$ carrier was added to the $CH_2Cl_2$ dispersion which was further stirred. The mixture of the $ZrO_2$ carrier and the dispersion was then dried in vacuo and subjected to firing in air in an electric furnace at 300° C. for 4 hours. Accordingly the $Au_{11}$ complex clusters were supported onto the $ZrO_2$ carrier to obtain a gold complex compound-carrying substance.

(Oxygen Plasma Processing for Removal of Organic Ligand)

The obtained gold complex compound-carrying substance was subjected to oxygen plasma processing prior to firing in air to remove the organic ligand from the gold complex compound, thereby obtaining a gold cluster catalyst containing gold atom clusters supported on the carrier.

The oxygen plasma processing was carried out using the device shown in FIG. 1 under the following conditions:
Oxygen Plasma Processing Conditions:
Time: 2 minutes
Sample mass: 0.2 g
Frequency: 29 kHz
Voltage: 65 V
Input power: 2.4 W The obtained gold cluster catalyst was subjected to high-angle annular dark field scanning transmission electron microscopy (HAADF-STEM) in order to examine whether or not a desired gold cluster catalyst was obtained.

The microscopy was carried out according to the following procedures.

The obtained gold cluster catalyst was first dispersed in a mixed solution (1:1, weight ratio) of ethanol and a dichloromethane solution to obtain a dispersion. The dispersion (one drop) was placed on a copper grid which was then dried in vacuo overnight at room temperature in a desiccator. Carbon was deposited three times on the grid. For HAADF-STEM, a microscope of a trade name "JEM-3200FS" (available from JEOL Ltd.) was used.

As a result, the average particle diameter was 0.8±0.4 nm.

Figure 2:
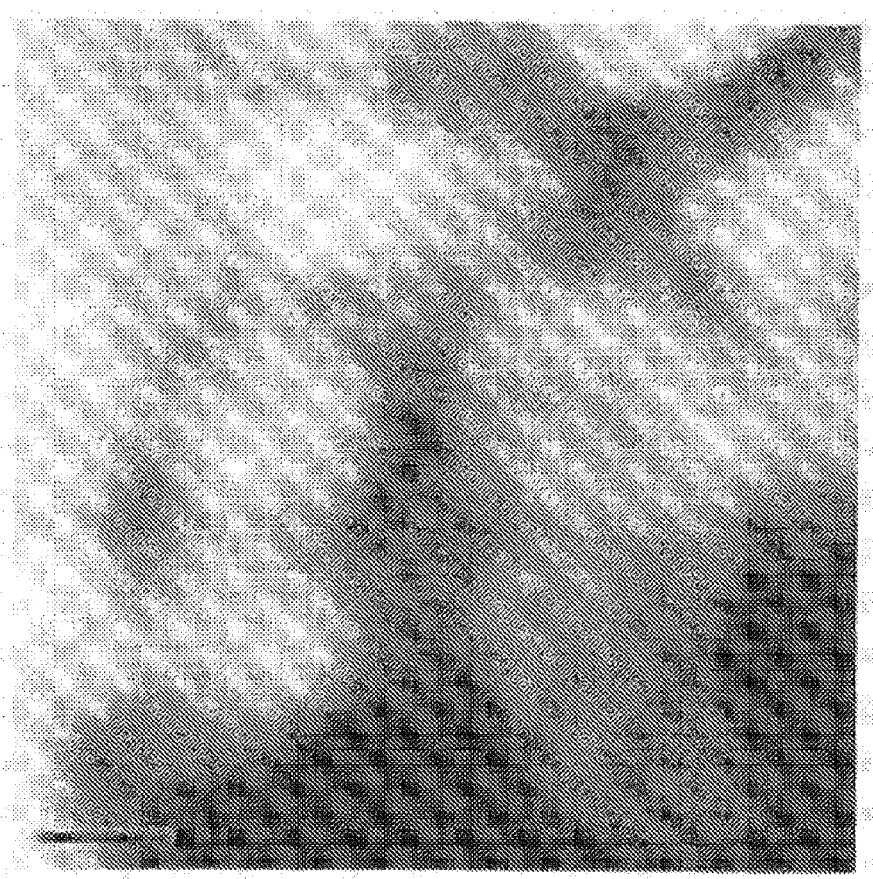
FIG. 2 is an electron micrograph (drawing-substituting photograph) of a gold cluster catalyst obtained in Example 1.
Figure 3:
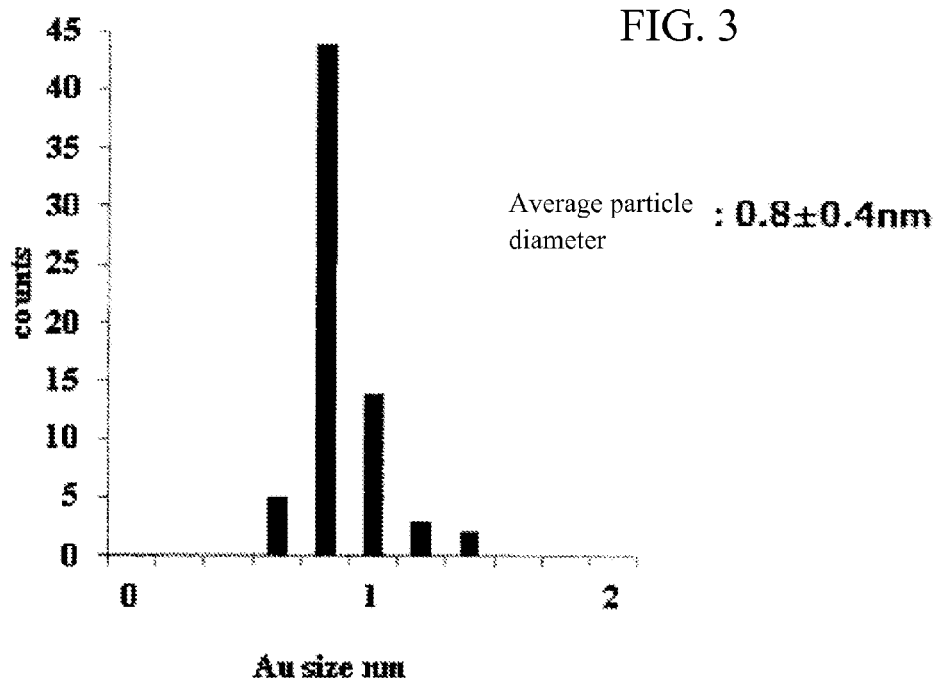
FIG. 3 is a histogram showing the size of gold clusters obtained in Example 1.

An electron micrograph of the particles is shown in FIG. 2 and a histogram illustrating the size of gold clusters is shown in FIG. 3.

Figure 4:
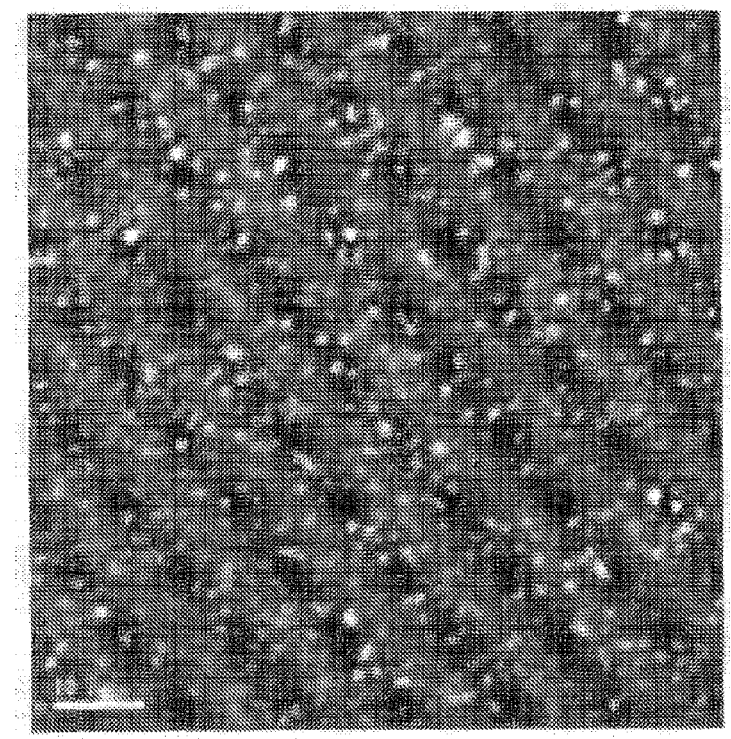
FIG. 4 is an electron micrograph (drawing-substituting photograph) of phosphine-protected Au clusters obtained as an intermediate in Example 1.
Figure 5:
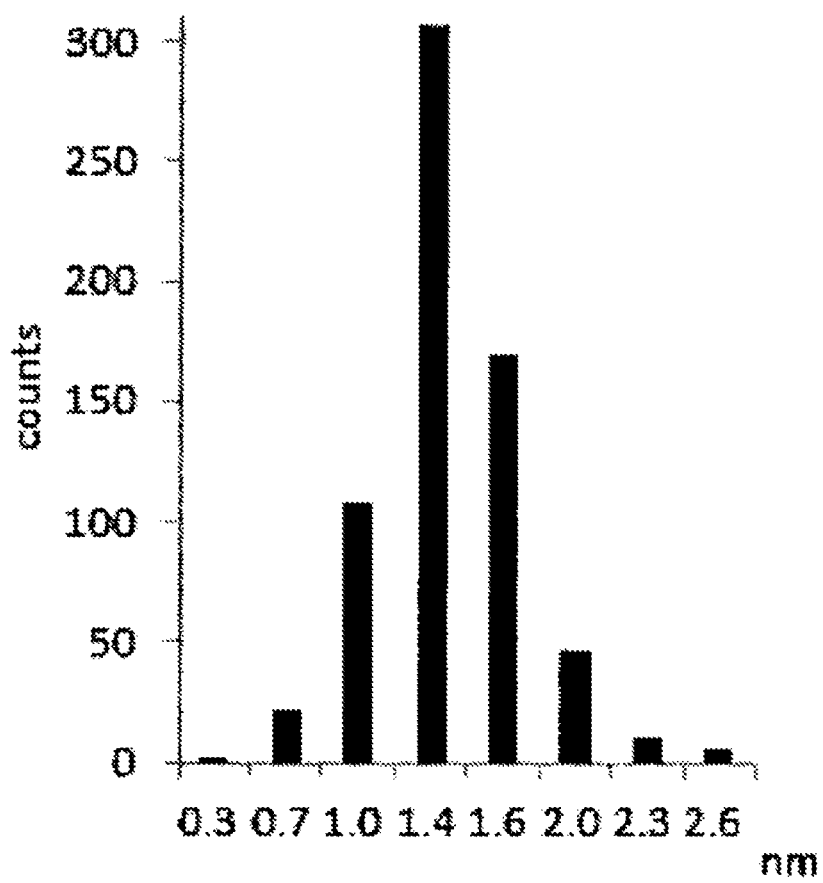
FIG. 5 is a histogram showing the size of phosphine-protected Au clusters obtained as an intermediate in Example 1.

Separately, for the phosphine-protected $Au_{11}$ clusters, an electron micrograph is similarly shown in FIG. 4 and a histogram illustrating the size of gold clusters is shown in FIG. 5.

In order to examine the removal of the organic ligand adsorbed on the surface of the obtained gold cluster catalyst, FT-IR diffuse reflectance spectroscopy was carried out.

FT-IR was carried out with a device of a trade name of "JASCO FT-IR-6100" (available from JASCO Corporation).

The conditions for measurements were as follows:
Scans: 200 times
Resolution: 2 $cm^{-1}$
As the background, a mirror cell was used.

Figure 6:
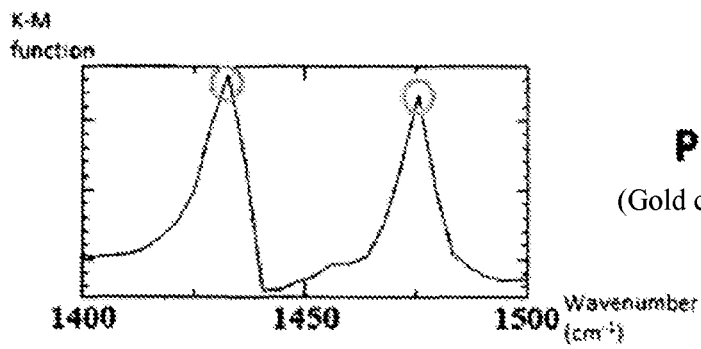
FIG. 6 shows FT-IR charts of gold cluster catalysts obtained in Examples 1 and 7.
Figure 6:
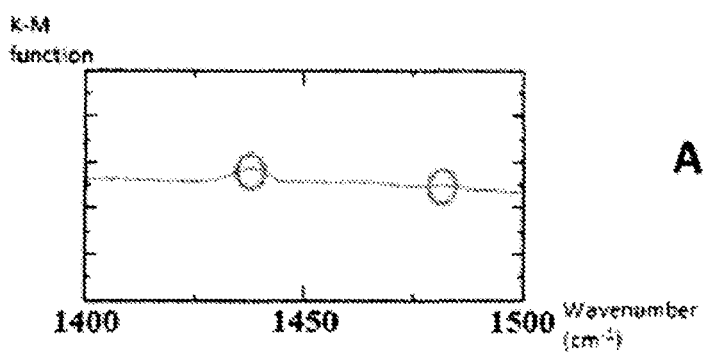
Figure 6:
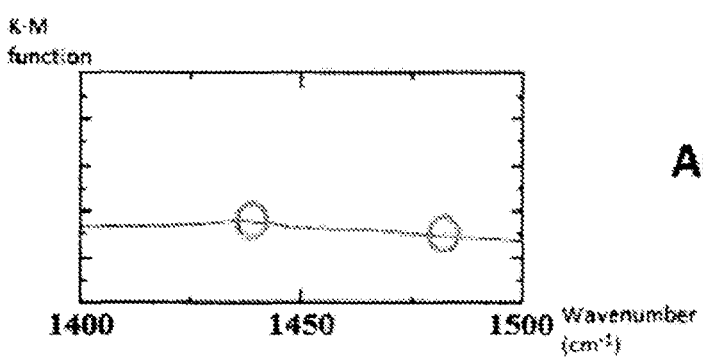

The resulting diffuse reflective spectrum was converted by the Kubelka-Munk (KM) function to the KM absorption spectrum corresponding to the transmission spectrum. The removal of the organic ligand was examined by observing the peaks due to C—H stretching vibrations in FT-IR. As a result, removal of organic ligand was confirmed. The obtained results of FT-IR are shown in FIG. 6. The result from the gold complex compound-carrying substance before oxygen plasma processing is also shown in FIG. 6. From these results, it is indicated that 95% or more organic ligand was removed.

Example 2

Preparation of Gold Cluster Catalyst Having the Number of Gold Atoms of 55

Figure 7:
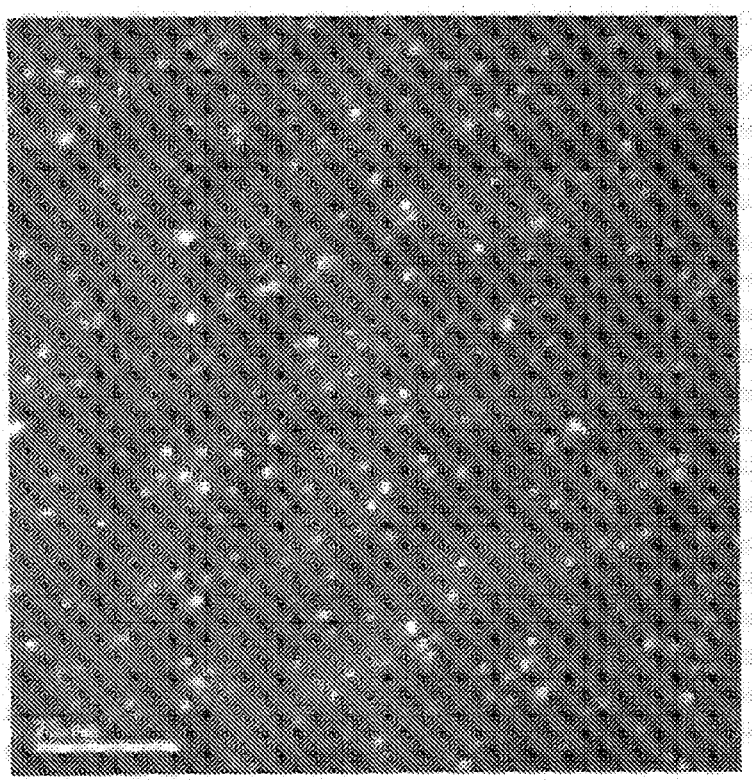
FIG. 7 is an electron micrograph (drawing-substituting photograph) of phosphine-protected Au clusters obtained as an intermediate in Example 2.
Figure 8:
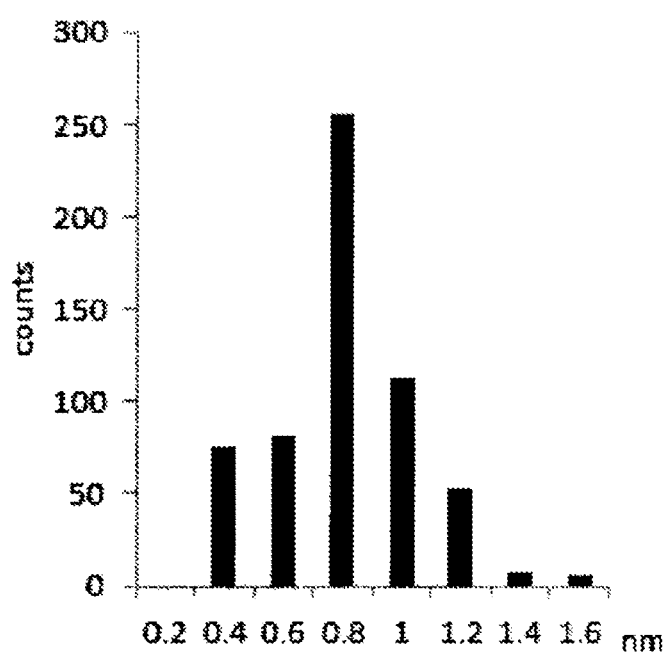
FIG. 8 is a histogram showing the size of phosphine-protected Au clusters obtained as an intermediate in Example 2.

A gold cluster catalyst was obtained in the same manner as in Example 1 except that Au clusters were prepared as described hereinbelow. An electron micrograph of phosphine-protected $Au_{55}$ clusters is shown in FIG. 7 and a histogram illustrating the size of gold clusters is shown in FIG. 8.

(Synthesis of $Au_{55}$ Clusters)

Chloro(triphenylphosphine)Au (I) (0.25 g) prepared in the same manner as in Example 1 was dissolved in 20 ml of benzene in a nitrogen atmosphere while stirring. To the solution, 3 ml of a solution of borane-tetrahydrofuran (THF) complex ($BH_3$-THF complex) was added dropwise in a nitrogen atmosphere at room temperature over 2 hours while stirring to obtain a product. The product was added to 5 ml of a dichloromethane solution, filtered and dried. The product was gradually added with 120 ml of pentane, filtered and dried to obtain the final product ($Au_{55}$ clusters).

Example 3

Preparation of Gold Cluster Catalyst Having the Number of Gold Atoms of 101

Figure 9:
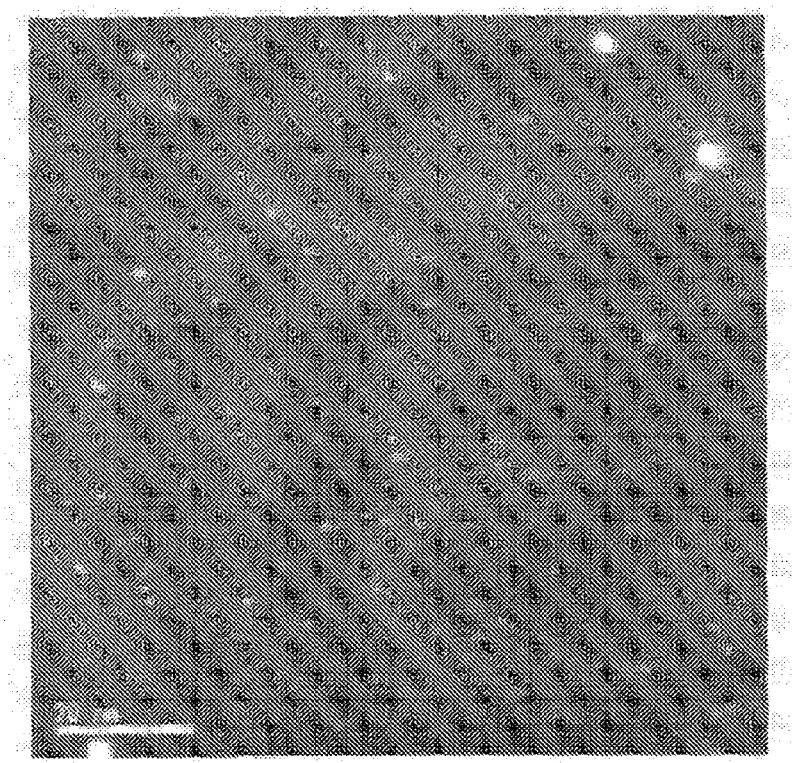
FIG. 9 is an electron micrograph (drawing-substituting photograph) of phosphine-protected Au clusters obtained as an intermediate in Example 3.
Figure 10:
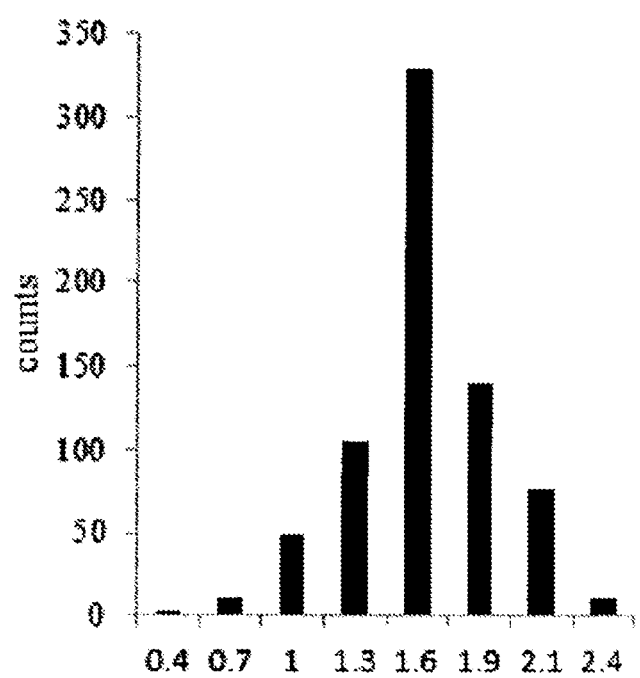
FIG. 10 is a histogram showing the size of phosphine-protected Au clusters obtained as an intermediate in Example 3.

A gold cluster catalyst was obtained in the same manner as in Example 1 except that Au clusters were prepared as described hereinbelow. An electron micrograph of phosphine-protected $Au_{101}$ clusters is shown in FIG. 9 and a histogram illustrating the size of gold clusters is shown in FIG. 10.

(Synthesis of $Au_{101}$ Clusters)

A solution (50 ml, solution (a)) of chloroauric acid (2.54 mmol) in distilled water and a solution (65 ml, solution (b)) of tetraoctylammonium bromide (TOAB) (2.93 mmol) in toluene were prepared. The prepared solution (a) and solution (b) were mixed in a nitrogen atmosphere over 30 minutes and reaction was allowed to proceed. Because the gold salt produced by the reaction had moved from an aqueous layer to a toluene layer, water was removed from the solution with a 50-ml syringe followed by vigorous shaking at room temperature. After 30 minutes, triphenylphosphine (8.85 mmol) was added to the solution to allow reaction to proceed. The color of the solution was changed from dark red to pale yellow within 5 minutes from the initiation of the reaction and further to opaque white after 1 hour. Subsequently a solution of sodium boronhydride (37.3 mmol) in distilled water (6 ml) was immediately added to the solution and the reaction was allowed to proceed while stirring at room temperature for 180 minutes to obtain a product. Pentane (125 ml) was added to the product which was then re-crystallized and dried to give the final product ($Au_{101}$ clusters).

Examples 4 to 6

Preparation of Gold Cluster Catalysts Including Ceria as a Carrier $Au_{11}$, $Au_{55}$ and $Au_{101}$ gold cluster catalysts were prepared in the same manners as respectively in Examples 1 to 3 except that the carrier used was $CeO_2$-1 instead of $ZrO_2$. The resulting gold cluster catalysts respectively had a removal rate of the organic ligand of 90% or more.

Examples 7 to 9

$Au_{11}$, $Au_{55}$ and $Au_{101}$ gold cluster catalysts were prepared in the same manners as respectively in Examples 1 to 3 except that the following firing treatment was carried out after the oxygen plasma processing. The removal rate of the organic ligand was 90% or more.
<Firing Treatment>
A gold cluster catalyst after the oxygen plasma processing was placed in an electric furnace and firing was carried out at 150° C. for 2 hours.

The catalyst obtained in Example 7 was subjected to FT-IR in the same manner as in Example 1. The result is shown in FIG. 6. The result indicates that 95% or more organic ligand was removed.

Examples 10 to 12

$Au_{11}$, $Au_{55}$ and $Au_{101}$ gold cluster catalysts were prepared in the same manners as respectively in Examples 7 to 9 except that the carrier used was $CeO_2$-1 instead of $ZrO_2$ and the firing temperature was 300° C. The resulting gold cluster catalysts respectively had a particle diameter of gold clusters of 2 nm or less and a removal rate of the organic ligand of 90% or more.

Test Example 1

One-Pot Synthesis of Azobenzene

A liquid phase reaction vessel for a catalyst used was an autoclave. In the autoclave, each catalyst (0.3 mol % of Au based on a substrate) obtained in Examples 1 to 12 was placed and 0.5 mmol of a substrate, nitrobenzene, 50 µL of an internal standard, dodecane, and 3 mL of a solvent were added. The autoclave was pressurized with 0.5 MPa of hydrogen and reaction was allowed to proceed at 60° C. for 6 hours. The solution after the reaction was filtered through a 0.45-µm membrane filter. The filtered solution was subjected to a quantitative analysis on Agilent 7890AGC (gas chromatography, trade name, available from Agilent). The results showed high catalytic activity for all catalysts.

Test Example 2

Hydrogenation of Cinnamaldehyde

Each of the catalysts (1 mol % of Au based on a substrate (calculated: 1 mol %, actual: 0.6 mol %)) obtained in Examples 6 and 12 was placed in an autoclave as a reaction vessel and 0.5 mmol of a substrate, cinnamaldehyde, 25 µL of an internal standard, anisole, and 3 mL of a solvent were added. The autoclave was pressurized with 0.5 MPa of hydrogen and the reaction was allowed to proceed at 80° C. for 22 (25) hours. The solution after the reaction was filtered through a 0.45-µm membrane filter. The obtained filtrate was subjected to a quantitative analysis on Agilent 7890AGC (gas chromatography, trade name, available from Agilent). The results are shown in FIG. 11.

As a comparison, a substance without oxygen plasma processing or firing treatment was examined for the catalytic activity. The result thereof is shown together.

Figure 11:
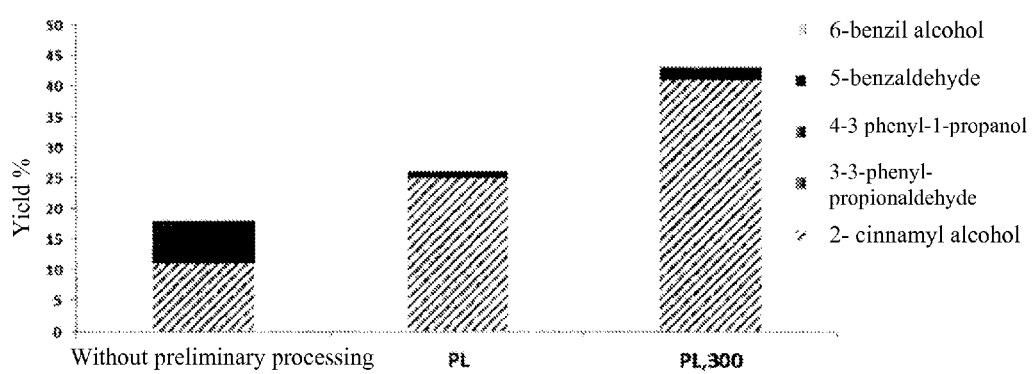
FIG. 11 is a bar graph showing the results of the catalytic activity test of catalysts obtained in Examples.

In FIG. 11, the comparison is indicated as "Without preliminary processing", the catalyst of Example 6 is indicated as "PL" and the catalyst of Example 12 is indicated as "PL, 300".

From the results shown in FIG. 11, it was found that the gold cluster catalyst of the present invention obtained after the oxygen plasma processing (the catalyst obtained in Example 6) had high selectivity of cinnamyl alcohol which was 83% at maximum. The catalyst obtained after the oxygen plasma processing and the treatment in air at 300° C. (the catalyst obtained in Example 12) had the highest conversion rate of cinnamaldehyde and also had high selectivity of cinnamyl alcohol.

Test Example 3

Hydrogenation of Nitrobenzene

Each of the catalysts (1 mol % of Au based on a substrate) obtained in Examples 1 and 7 was placed in an autoclave and 0.5 mmol of a substrate, nitrobenzene, 50 µL of an internal standard, dodecane, and 3 mL of a solvent, toluene, were added. The autoclave was pressurized with 0.5 MPa of hydrogen and the reaction was allowed to proceed at 60° C. for 6 hours. The solution after the reaction was filtered through a 0.45-µm membrane filter. The obtained filtrate was subjected to a quantitative analysis on Agilent 7890AGC. The results are shown in FIG. 12.

As a comparison, a substance without oxygen plasma processing or firing treatment was examined for the catalytic activity. The result thereof is shown together.

Figure 12:
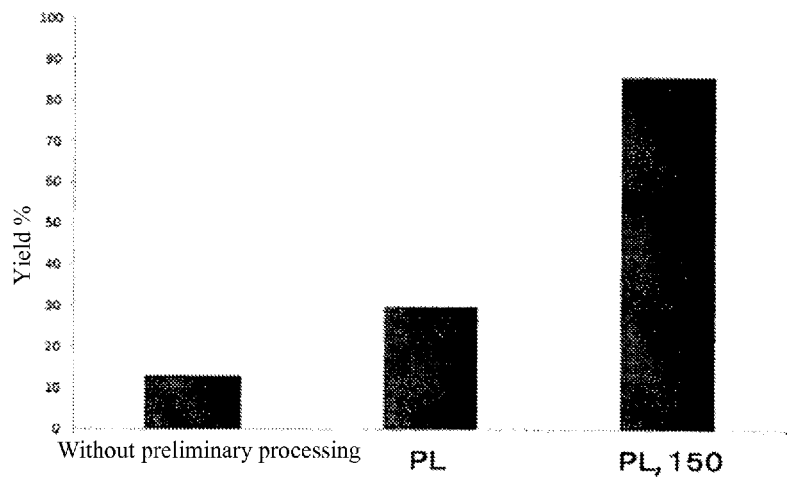
FIG. 12 is a bar graph showing the results of the catalytic activity test of catalysts obtained in Examples.

In FIG. 12, the comparison is indicated as "Without preliminary processing", the catalyst of Example 1 is indicated as "PL" and the catalyst of Example 7 is indicated as "PL, 150".

As apparent from the results shown in FIG. 12, the gold catalysts of the present invention (particularly Example 7) showed high catalytic activity.

The invention claimed is:
1. A method of producing the gold catalyst comprising clusters of gold atoms on a carrier, the method comprising steps of:

mixing a carrier and a plurality of gold cluster compounds wherein each of the gold cluster compound has a predetermined number of gold atoms that are stabilized by an organic ligand;

subjecting the mixture of the carrier and the gold cluster compounds to an oxygen plasma treatment; and firing the mixture in air at a temperature ranging of 100° C. to 800° C. to form the gold catalyst comprising the carrier and clusters of gold atoms, wherein the number of the gold atoms in each of the clusters is selected from the group consisting of 11, 13, 55, 101 and 147.

* * * * *